United States Patent [19]

Juvinall et al.

[11] Patent Number: 4,945,228
[45] Date of Patent: Jul. 31, 1990

[54] INSPECTION OF CONTAINER FINISH

[75] Inventors: John W. Juvinall, Ottawa Lake, Mich.; James A. Ringlien, Maumee, Ohio

[73] Assignee: Owens-Illinois Glass Container Inc., Teledo, Ohio

[21] Appl. No.: 327,662

[22] Filed: Mar. 23, 1989

[51] Int. Cl.$^5$ .............................................. G01N 9/04
[52] U.S. Cl. .................................. 250/223 B; 356/240
[58] Field of Search ............... 250/223 B, 223 R, 560, 250/563, 566, 572; 356/237, 240; 358/106

[56] References Cited

U.S. PATENT DOCUMENTS

| | | | |
|---|---|---|---|
| 3,880,750 | 4/1975 | Butler et al. | 356/240 |
| 4,378,493 | 3/1988 | Dorf et al. | 250/223 B |
| 4,378,494 | 3/1983 | Miller | 250/223 B |
| 4,378,495 | 3/1983 | Miller | 250/223 B |
| 4,454,542 | 6/1984 | Miyazawa | 358/106 |
| 4,644,151 | 2/1987 | Juvinall | 250/223 B |
| 4,701,612 | 10/1987 | Sturgill | 250/223 B |

Primary Examiner—David C. Nelms

[57] ABSTRACT

Apparatus for inspecting the sealing surface of a container finish that includes a light source positioned to direct light energy onto the container sealing surface as the container is held in stationary position and rotated about its central axis. A camera that includes an array of light sensitive elements is positioned and oriented with respect to the container axis of rotation to receive light energy reflected by the sealing surface, with the camera having an effective field of view limited to an angular portion less than the entire circumference of the container sealing surface. The camera array is scanned at increments of container rotation to develop information indicative of intensity of light at each array element as a function of such increments, and commercial variations in the container sealing surface are detected as a function of such information. The camera array is oriented with respect to the container axis of rotation and coupled to the scanning mechanism to scan the array in linear fields orthogonal to the axis of rotation, and scan information is stored for subsequent analysis in two-dimensional electronic memory as a function of array element and scan increment. The light source is strobed at increments of container rotation and the camera array, which may be either a linear array or an area array, is scanned at each strobe increment of container rotation.

43 Claims, 4 Drawing Sheets

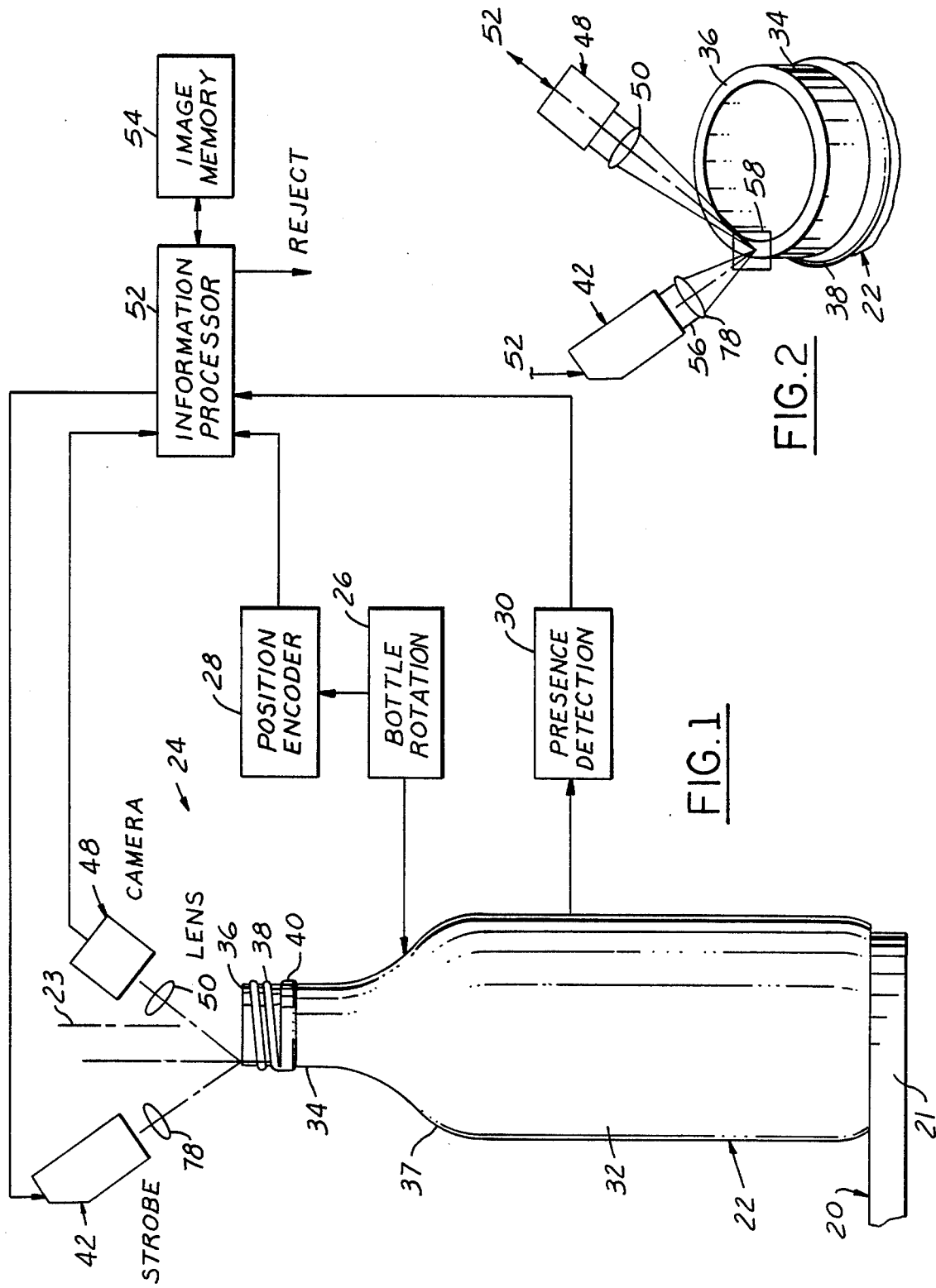

INSPECTION OF CONTAINER FINISH

The present invention is directed to optical imaging apparatus having particular utility for inspection of containers, and more specifically to an apparatus and method for inspecting the finish of containers for commercial variations and geometric characteristics.

BACKGROUND OF THE INVENTION

In the art of container manufacture, the term "container finish" generally refers to that portion of the container that defines the container mouth. In a bottle, for example, the finish includes that portion of the container neck having threads and/or shoulders for receiving the container cap, as well as the upper surface of the neck surrounding the container mouth against which the cap seats. It is important that the container finish be properly manufactured so that a cap may be affixed thereto to seal the container cavity against leakage and escape of carbonation during handling and storage.

Conventional technology for mass production of glass or plastic containers involves forming the containers in a multiplicity of molds. Various types of faults or checks, termed "variations" in the art, may occur. It has heretofore been proposed to employ optical scanning techniques for inspecting such containers for variations that affect optical transmission characteristics of the container. In U.S. Pat. Nos. 4,378,493, 4,378,494 and 4,378,495, all of which are assigned to the assignee of the present application, there are disclosed methods and apparatus in which glass containers are conveyed through a plurality of stations where they are physically and optically inspected. At one inspection station, a glass container is held in vertical orientation and rotated about its vertical axis. An illumination source directs diffused light energy through the container sidewall. A camera, which includes a plurality of light sensitive elements or pixels oriented in a linear array parallel to the vertical axis of container rotation, is positioned to view light transmitted through a vertical strip of the container sidewall. The output of each pixel is sampled at increments of container rotation, and event signals are generated when adjacent pixel signals differ by more than a preselected threshold level. An appropriate reject signal is produced and the rejected container is sorted from the conveyor line.

U.S. Pat. No. 3,880,750, likewise assigned to the assignee hereof, discloses an electro-optical gauge specifically adapted for inspecting the sealing surface of a container finish. A light source is positioned above the container and directs a light beam at constant intensity downwardly onto the sealing surface as the container is rotated. A camera has a single sensor positioned to receive light energy reflected by the sealing surface and provides an analog output to associated scanning electronics. The sensor output is monitored as the container is rotated about its axis, and commercial variations at the sealing surface, such as line-over-finish or LOF variations, open or closed blisters and unfilled finish variations, are detected as a function of variations in sensor output amplitude.

U.S. Pat. No. 4,701,612, assigned to the assignee hereof, discloses a method and apparatus for inspecting the finish of transparent containers, particularly glass containers, that include facility for directing diffused light energy laterally through the container finish as the container is rotated about its central axis. A camera includes a plurality of light sensitive elements or pixels disposed in a linear array angulated with respect to the container axis and coplanar therewith to view the external and internal finish wall surfaces, the latter through the open canister mouth. Individual elements of the camera linear array are sampled by an information processor at increments of container rotation, and corresponding data indicative of light intensity at each element is stored in an array memory as a combined function of element number and scan increment. Such data is compared, following completion of container rotation, to standard data indicative of an acceptable container finish, and a reject signal is generated if such comparison exceeds an operator-adjustable threshold.

U.S. Pat. No. 4,454,542 discloses apparatus for inspecting the sealing surface of containers in which an annular light source is positioned above and coaxial with the container mouth to direct light energy through a diffuser onto the sealing surface. A camera is positioned above and coaxial with the light source and container to view the sealing surface through the central opening of the light source. The camera includes a CCD area array of light sensitive elements that receives the entire image of the container sealing surface as the container is held stationary. The area image is scanned to identify commercial variations as a function of light reflected from the sealing surface.

OBJECTS AND SUMMARY OF THE INVENTION

One problem that is characteristic of prior art sealing-surface inspection apparatus of the described character lies in distinguishing between line-over-finish or LOF variations, which can deleteriously affect sealing capabilities, and "dirty" finishes that affect sealing surface light reflectivity but do not seriously affect sealing capabilities. A general object of the present invention, therefore, is to provide apparatus for electro-optically inspecting the sealing surface of containers that will detect, discriminate and measure radial LOF variations, non-radial LOF variations, closed blisters, open blisters, rolled-in finishes, unfilled finishes, wire edges and dirty finishes.

Another problem not adequately addressed in the art lies in use of conventional inspection apparatus in conjunction with caps and containers of current manufacture. Specifically, many conventional bottle caps have a liner that so engages the container mouth that a major portion of the sealing effect is obtained at the inside diametric edge of the mouth. Press-and-blow molding machines of current design produce containers that have a step-down shoulder at this edge. Very small blisters in the sealing surface area tend to be soft on the inside surface edge. If such a blister opens during use, there can be a loss of seal within the container. A problem with sealing surface inspection devices of current design is that they do not adequately inspect the inside step-down shoulder of such containers for variations of the described character that may affect ability to seal the container cavity. Thus, another object of the present invention is to provide a sealing surface inspection apparatus that overcomes this problem and includes facility specifically for inspecting the step-down shoulder of the container sealing surface.

A more particular object of the present invention is to provide a container finish inspection apparatus that is adapted to detect commercial variations at the finish sealing surface of any orientation, and that is readily adjustable for inspection of containers having differing finish sizes.

Apparatus for inspecting the sealing surface of container finishes in accordance with the presently preferred embodiments of the invention includes a light source positioned to direct light energy onto the container sealing surface as the container is rotated about its central axis. A camera that includes an array of light sensitive elements is positioned and oriented with respect to the container axis of rotation to receive light energy reflected by the sealing surface, with the camera having an effective field of view limited to an angular portion less than the entire circumference of the container sealing surface. The camera array is scanned at increments of container rotation to develop information indicative of intensity of light at each array element as a function of such increments, and commercial variations in the container sealing surface are detected as a function of such information. Preferably, the camera array is oriented with respect to the container axis of rotation and coupled to the scanning mechanism to scan the array in linear fields orthogonal to the axis of rotation, and scan information is stored for subsequent analysis in two-dimensional electronic memory as a function of array element and scan increment. The light source is strobed at increments of container rotation and the camera array, which may be either a linear array or an area array, is scanned at each strobe increment of container rotation.

Thus, in accordance with this aspect of the invention, individual pixel information is obtained over the entire sealing surface by scanning the camera array at increments of container rotation and storing the individual pixel information bytes in an array memory. The individual information bytes can then be processed, using any suitable technique, for greatly enhanced resolution in detecting and distinguishing among a wide variety of surface conditions, including both unacceptable commercial variations and variations that are acceptable but should be addressed.

In accordance with a second important aspect of the present invention, the light source comprises a multiplicity of light emitting elements mounted in a spherical array that has a center of focus spaced from the array. The image of the array center is focused substantially at the container sealing surface, preferably by Fresnel lenses. A diffuser is positioned at the array center focus, which effectively smooths light intensity between the array elements to obtain a solid angle-beam of light energy focused substantially at the container sealing surface within the field of view of the camera array. The light elements preferably comprise LEDs (light emitting diodes) mounted in a part-spherical plate in an hexagonal close-packing arrangement.

BRIEF DESCRIPTION OF THE DRAWINGS

The invention, together with additional objects, features and advantages thereof, will be best understood from the following description, the appended claims and the accompanying drawings in which:

FIG. 1 is a schematic diagram of apparatus for inspecting the finish of containers in accordance with the present invention;

FIG. 2 is a schematic illustration of the container finish as illuminated by the light source and viewed by the camera of FIG. 1;

DETAILED DESCRIPTION OF PREFERRED EMBODIMENTS

Figure 3A:
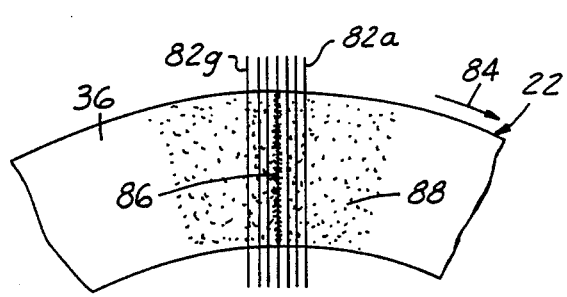
FIGS. 3A-3E are schematic diagrams that illustrate sealing surface images with various types of variations detected and distinguished in accordance with the present invention.

Referring to FIG. 1, a conveyor 20, typically including a starwheel (not shown) and a slide plate 21, is so disposed and connected to a source of molded containers as to bring successive containers 22 into position at a finish inspection station 24. Conveyor 20 may be of any suitable type, such as those shown in U.S. Patent Nos. 4,230,219 and 4,378,493, and would typically include a rotatable starwheel for bringing successive containers into position and holding the containers in fixed position during the scanning operation. A bottle rotating device 26, such as a drive roller, is positioned to engage container 22 at station 24 and to rotate the container about its central axis 23. An encoder 28 is coupled to the container rotation mechanism to provide signals indicative of increments of container rotation. A detector 30, such as a switch, is positioned to provide a signal indicative of presence of container 22 at station 24.

In the preferred implementation of the invention herein discussed, container 22 is illustrated as a molded glass bottle having a container body 32 and a generally cylindrical neck 34 that projects upwardly from the body shoulder 37. The finish portion of the container includes an upper portion of neck 34 that terminates in a cap sealing surface 36 inspected in accordance with the present invention. A helical thread 38 is integrally molded into the outer surface of the finish wall that surrounds the container mouth, and a lip or shoulder 40 is likewise formed on the finish wall outer surface over which a cap skirt may be crimped in the usual manner for affixing the cap to the container. In general, the present invention is disclosed in conjunction with apparatus adapted to inspect the sealing surface 36 against which the cap seals.

A light source 42 (FIGS. 1, 2 and 11) is positioned to direct light energy downwardly onto surface 36 from a direction at an angle to axis 23. A camera 48 is positioned with respect to light source 42 to receive light reflected from sealing surface 36 and forms an image of the sealing surface on a light sensitive array in camera 48 through a lens 50. An information processor 52 receives signals from detector 30 indicating presence of a container 22 at inspection station 24, and signals from encoder 28 indicative of increments of container rotation. Camera 48 is likewise coupled to information processor 52 for receiving scan control signals and providing signals indicative of intensity of light incident on the camera from surface 36 and light source 42. Light source 42 is likewise controlled by processor 52. Information processor 52 is connected to an image memory 54, and has an output for providing a reject signal to container sorting apparatus (not shown).

Figure 11:
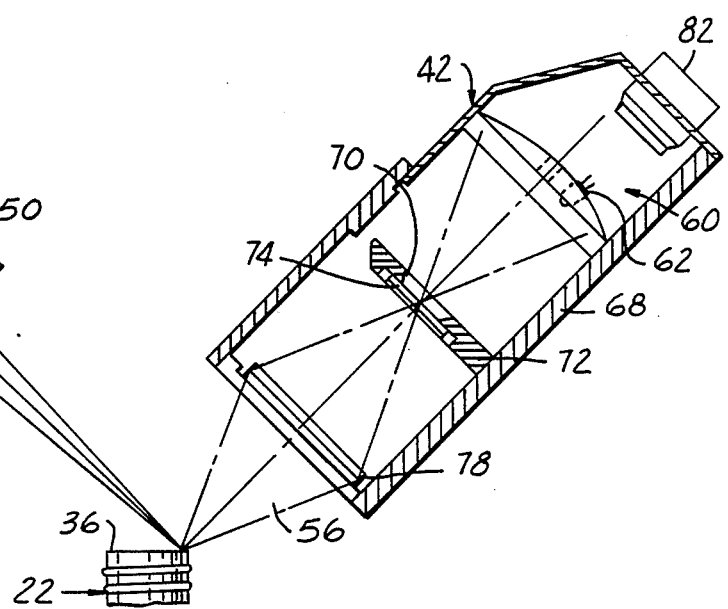
FIG. 11 is a partially sectioned side elevational view that illustrates the camera and light source in accordance with a preferred embodiment of the invention.

In accordance with an important feature of the present invention illustrated in FIGS. 2 and 11, light source 42, which preferably comprises a stroboscopic light source energized by information processor 52 at increments of container rotation, focuses a cone 56 of light energy of substantial solid angle onto a limited circumferential portion of container sealing surface 36, and camera 48 with its lens 50 has a limited field of view, viewing substantially only the illuminated portion 58 (FIG. 2) of the sealing surface. Light source 42 is illustrated in greater detail in FIGS. 11-13 as comprising an array 60 of individual LEDs 62 mounted in corresponding individual openings 64 of a part-spherical plate 66. Plate 66 is mounted within a shell 68 so as to position the center of curvature of array 60 at an aperture 70 in a shell end wall 72. A diffuser 74 is mounted on wall 72 at aperture 70. Light energy from spherical array 60, projected through aperture 70 and diffuser 74, is directed through Fresnel lenses 78 onto sealing surface 36 of container 22. Light energy reflected by surface 36 is directed by camera lenses 50 into camera 48, which includes an optical detector 80 in the form of a CCD array of light sensitive elements constructed and arranged to be scanned by information processor 52 (FIG. 1) in a direction orthogonal to the axis of container rotation. A connector 82 on shell 42 provides connection to information processor 52 for strobing LEDs 62.

Figure 12:
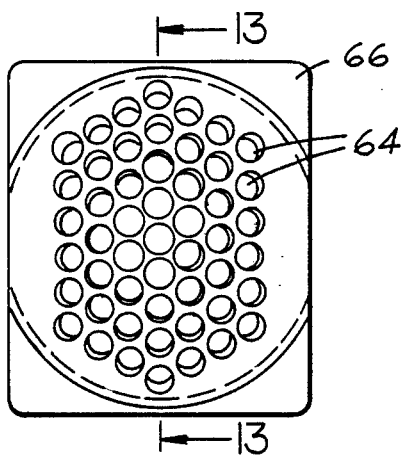
FIG. 12 is an end elevational view of the LED mounting plate in the light source of FIG. 11.
Figure 13:
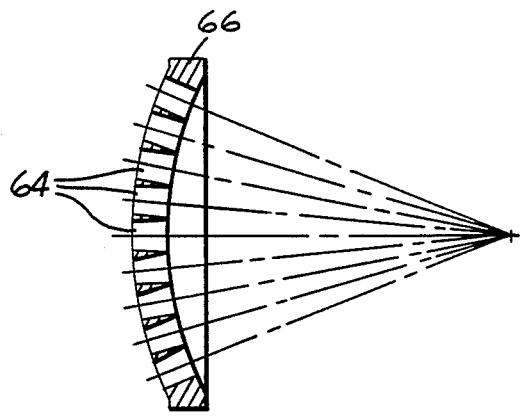
FIG. 13 is a sectional view taken substantially along the line 13—13 in FIG. 12.

Stroboscopic light source 42 has the advantage of low-voltage operation, as compared with conventional xenon strobes. The solid state LEDs 62 possess greater operating life and reliability than do conventional xenon strobes. The cone angle of beam 56 is sufficiently large that normal variations and roughness at the sealing surface are not detected as commercially significant variations. Diffuser 74 smooths the beam wavefront for effectively filling the gaps between the diodes, which preferably are carried in a close-packed hexagonal arrangement as illustrated in FIG. 12. It will also be appreciated that intensity gradients as a function of angle can be approximated by driving rows or regions of the LEDs 62 at differing voltage levels. Thus, variations in brightness at the sealing surface as a function of angle can be deliberately produced to enhance detection of and discrimination among various types of commercial variations.

Figure 4:
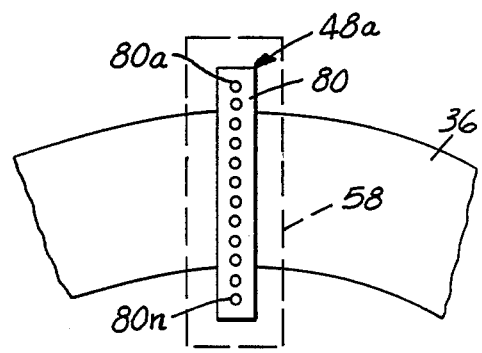
FIGS. 4 and 5 are schematic diagrams that illustrate sealing surface images at the camera in accordance with two embodiments of the invention.

FIG. 4 illustrates the field of view 48a of camera 48 within illuminated area 58 where array 80 comprises a linear array of light sensitive elements 80a-80n oriented in a direction orthogonal to the tangent of the sealing surface at the point of inspection. Light source 42 (FIGS. 1, 2 and 11) is strobed and array 80 is simultaneously scanned at preselected increments of container rotation, with information indicative of light intensity reflected by sealing surface 36 and received at each array element 80a-80n being stored in image memory 54 (FIG. 1) as a function of scan increment. Thus, array memory 54 in this example comprises an N×M array memory, where N is equal to or greater than the number of elements or pixels 80a-80n in array 80, and M is equal to or greater than the number of scan increments for one complete rotation of container 22. In a modification to the embodiment of FIG. 4, light source 42 may comprise a bright continuously illuminated source, with the speed of scanning array 80 being sufficient to develop stop-action images of the container sealing surface.

Figure 3B:
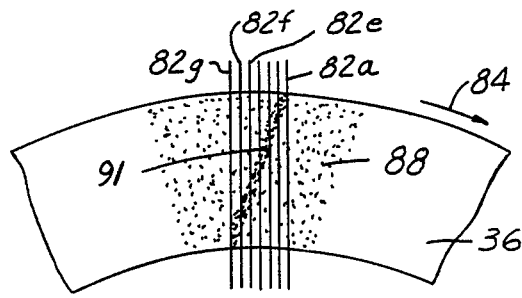
Figure 3C:
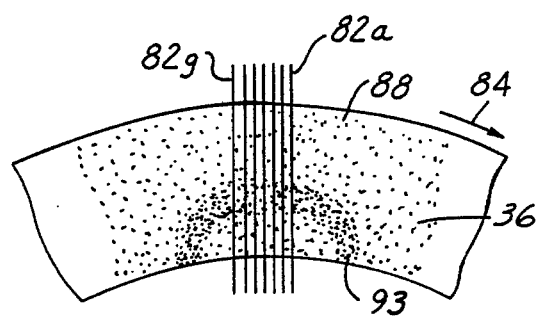
Figure 3D:
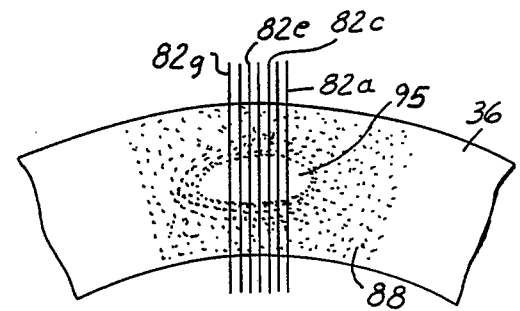
Figure 3E:
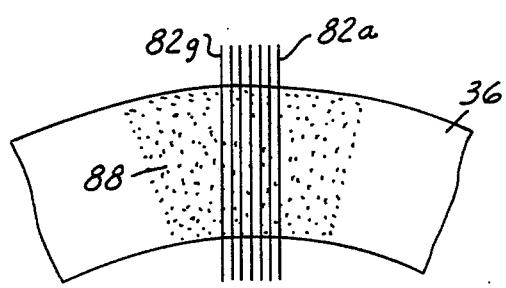

FIGS. 3A-3E illustrate five exemplary types of commercial variations detected by camera 48 and information processor 52. For purposes of illustration only, seven successive scans 82a-82g are shown in each FIG. 3A-3E. These scan lines represent successive scan increments with respect to the direction of container rotation 84. A radial line-over-finish (LOF) variation is viewed by camera 48 as a dark line 86 that covers one or more of the scans 82a-82g, depending upon circumferential width, surrounded by a field of gray 88. On the other hand, a non-radial LOF variation is illustrated in FIG. 3B as being viewed as a dark line 91 that angularly intersects and cuts across severed scan lines 82a-82g. An open blister is illustrated in FIG. 3C as an arcuate dark zone 93 where light energy incident on the blister sidewalls is reflected thereby away from camera 48, surrounded by a field of gray. On the other hand, a closed blister is viewed as a white spot 95 (FIG. 3D) surrounded by a field of gray 88 because the closed blister enhances reflection of light energy to the camera through reflection off of the various blister surfaces. A dirty finish (FIG. 3E) appears as a substantially uniform gray or random black and white field 88, and does not affect sealing capabilities. The random black and white field can be analyzed and rejected as appropriate. Commercial variations of the type illustrated in FIGS. 3A-3E, as well as other commercial variations at the sealing surface, can be readily detected and discriminated on the basis of such images, electro-optically obtained and stored in image memory 54, employing suitable conventional information processing and data analysis techniques.

Figure 5:
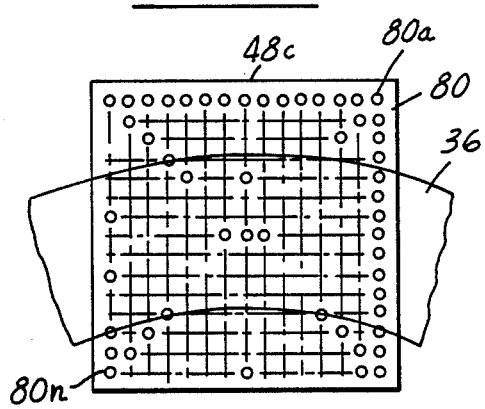
Figure 6:
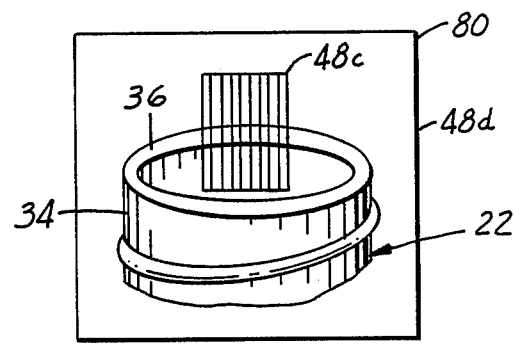
FIG. 6 is a schematic diagram that illustrates camera field of view in accordance with a third embodiment of the invention.

FIG. 5 illustrates another embodiment of the invention in which array 80 takes the form of an area array having rows and columns of elements 80a-80n projected by lens 50 (FIGS. 1, 2 and 11) to a field of view 48c over a limited circumferential portion of sealing surface 36. In this embodiment, one or more rows of camera elements 80a-80n are scanned at each strobe increment. Adjacent rows may be integrated for enhanced detection. There is thus developed, in effect, a series of still or stop-action images of surface 36. FIG. 6 illustrates an application of the embodiment of FIG. 5 in which field of view 48c is formed over a small segment of the overall camera array 80, which itself has an enlarged field of view 48d that includes the entire container finish 34. The embodiment of FIG. 6 has the particular advantage of being able to image the entire container finish during set up, for example, and thereafter being limited to the field of view 48c for sealing surface inspection and analysis purposes. Techniques for so limiting the effective field of view of a CCD array camera, as well as selectively scanning and integrating selected array rows, are disclosed in U.S. Application Ser. No. 245,236, filed Sept. 16, 1988 (Docket 16068) and assigned to the assignee hereof, the disclosure of which is incorporated herein by reference.

Figure 7:
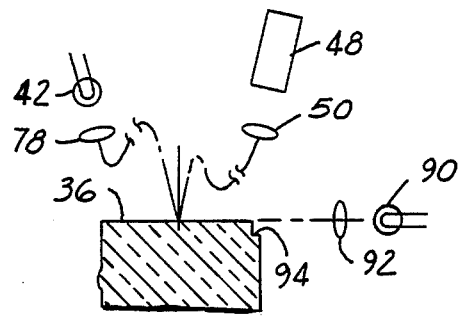
FIG. 7 is a fragmentary schematic diagram that illustrates apparatus for inspecting container sealing surface and inside step-down shoulder in accordance with a further embodiment of the invention.
Figure 8:
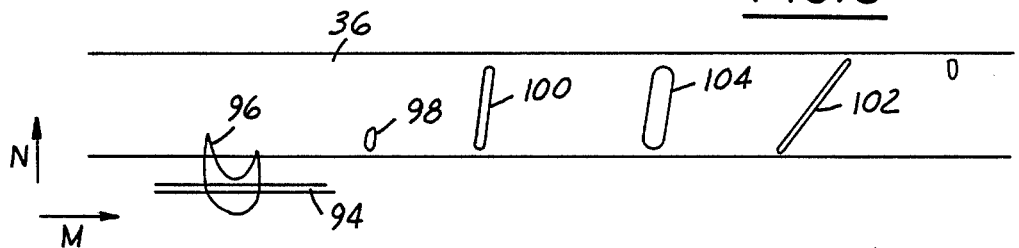
FIG. 8 schematically illustrates the unwrapped image viewed by the finish camera in the embodiment of FIG. 7.

FIG. 7 illustrates a modified embodiment of the invention in which a second light source 90 is positioned to focus light energy through a lens 92 onto the step-down shoulder 94 at the inside diameter of the container mouth, with camera 48 being positioned to receive energy normally reflected both by surface 36 and by the step-down shoulder 94. FIG. 8 is a schematic illustration of the corresponding image stored in memory 54 (FIG. 1) for a complete revolution of the container finish. A blister 96 extends from sealing surface 36 into step-down shoulder 94. Only a small portion of the blister actually appears in sealing surface 36, whereas the major portion of the blister lies at shoulder 94 and, if broken, may result in loss of seal. The second blister 98 in sealing surface 36 is small and tends to be harder, and thus no threat to the seal. However, it is again noted that, in the absence of the image of shoulder 94, blisters 96, 98 would appear substantially the same. Blister 100 is very narrow, and will tend to be hard and cause little threat to the seal. Blisters 100, 102 may be readily distinguished from blister 104, which presents more of a sealing problem.

Figure 9:
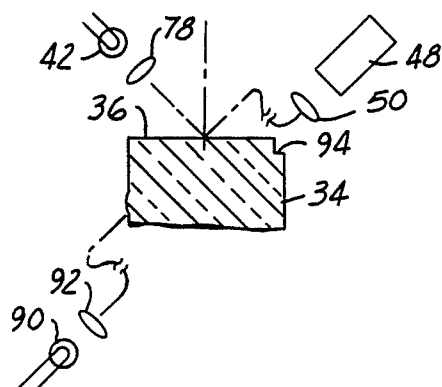
FIGS. 9 and 10 illustrate modified embodiments of the invention for inspecting the sealing surface and step-down shoulder.
Figure 10:
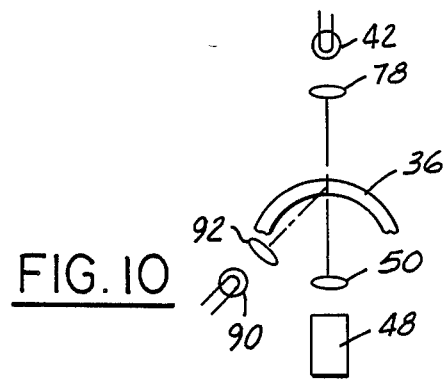

FIG. 9 illustrates a modification to the embodiment of FIG. 7 wherein second light source 90 and lens 92 are positioned to transmit light energy through container finish 34 and step-down shoulder 94 to lens 50 and camera 48. Blisters and other refractive variations direct light array from camera 48, and thus appear darker than normal. FIG. 10 illustrates another modification in which light source 90 that illuminates the internal step-down shoulder is positioned off-axis with respect to primary light source 42 and camera 48. Thus, the embodiment of FIG. 10 normally provides a dark-field of step-down shoulder 94, with blisters 96 (FIG. 8) functioning to reflect energy from source 90 to camera 48 for detection purposes.

We claim:

1. Apparatus for inspecting the finish of containers having a central axis and an open mouth surrounded by axially facing surface for sealing engagement with a container cap, said apparatus comprising:
   means for rotating the container about its central axis,
   a light source positioned to direct light energy onto the sealing surface of a container in said rotating means,
   a camera that includes an array of light sensitive elements, said light source and said camera being positioned at respective acute angles to said sealing surface such that light energy from said source is directly reflected by said sealing surface to said camera, said camera having an effective field of view limited to an angular portion less than the entire circumference of the container sealing surface,
   means for scanning said camera array at increments of container rotation to develop information indicative of intensity of light reflected by said sealing surface onto each said element as a function of said increments, and
   means for detecting commercial variations in the container sealing surface as a function of said information.

2. The apparatus set forth in claim 1 wherein said camera array is oriented with respect to said axis and coupled to said scanning means to scan said array in linear fields orthogonal to said axis.

3. The apparatus set forth in claim 2 wherein said scanning means includes means for storing said information in two-dimensional memory as a function of array element and scan increment.

4. The apparatus set forth in claim 3 further comprising means for strobing said light source at increments of container rotation.

5. The apparatus set forth in claim 4 wherein said camera comprises a linear array camera, and wherein said array is scanned and said light source is strobed at equal increments of container rotation.

6. The apparatus set forth in claim 4 wherein said camera comprises an area array camera, and wherein said scanning means comprises means for scanning a number of rows of said area array at each strobe increment of container rotation.

7. The apparatus set forth in claim 1 further comprising means for strobing said light source at increments of container rotation.

8. The apparatus set forth in claim 7 wherein said light source includes means for focusing a cone of light energy of substantial solid angle onto the container sealing surface within said field of view.

9. The apparatus set forth in claim 8 wherein said light source comprises a multiplicity of light emitting elements, means mounting said light elements in a spherical array having a center of curvature, and means for focusing an image of said center of curvature substantially at said container sealing surface.

10. The apparatus set forth in claim 9 wherein said focusing means comprises a Fresnel lens.

11. The apparatus set forth in claim 10 further comprising means for diffusing said light beam.

12. The apparatus set forth in claim 11 wherein said diffusing means is positioned at said center of curvature.

13. The apparatus set forth in claim 12 wherein said light elements comprise LEDs.

14. The apparatus set forth in claim 13 wherein said element-mounting means comprises means mounting said elements in an hexagonal close-packing arrangement.

15. The apparatus set forth in claim 1 wherein said light source comprises a multiplicity of light emitting elements, means mounting said light elements in a spherical array having a center focus, and means for focusing an image of said center focus substantially at said container sealing surface.

16. The apparatus set forth in claim 15 further comprising means for diffusing said light beam.

17. The apparatus set forth in claim 16 wherein said diffusing means is positioned at said center focus.

18. The apparatus set forth in claim 17 wherein said element-mounting means comprises means mounting said elements in an hexagonal close-packing arrangement.

19. The apparatus set forth in claim 18 wherein said focusing means comprises a Fresnel lens.

20. The apparatus set forth in claim 1 for inspecting a step-down shoulder at the inside diameter of the mouth sealing surface and further comprising a second light source illuminating said step-down shoulder within said camera field of view.

21. The apparatus set forth in claim 20 further comprising means for strobing said light sources simultaneously.

22. The apparatus set forth in claim 21 wherein said second light source is positioned to transmit light energy through the container finish onto said camera.

23. The apparatus set forth in claim 21 wherein said second light source is positioned to reflect light energy off of said step-down shoulder onto said camera.

24. Apparatus for inspecting a selected portion of a container having a central axis, said apparatus comprising: means for positioning a container at an inspection location, a light source for directing a cone of light energy of substantial solid angle onto said selected portion of a container in said positioning means, a camera positioned to have a field of view that includes that portion of the container illuminated by said light source, and means responsive to said camera for indicating optical characteristics of the container,
  characterized in that said light source comprises a multiplicity of light emitting elements, means mounting said light elements in a spherical array having a center of curvature, and means for focusing an image of said center of curvature substantially at said selected portion of said container.

25. The apparatus set forth in claim 24 further comprising means for diffusing said image.

26. The apparatus set forth in claim 25 wherein said diffusing means is positioned at said center of curvature.

27. The apparatus set forth in claim 26 wherein said element-mounting means comprises means mounting said elements in an hexagonal close-packing arrangement.

28. The apparatus set forth in claim 27 wherein said focusing means comprises a Fresnel lens.

29. The apparatus set forth in claim 28 wherein said light elements comprise LEDs.

30. The apparatus set forth in claim 24 wherein said positioning means includes means for rotating the container about its central axis, and wherein said apparatus further comprises means for strobing said light source at increments of container rotation.

31. A method of inspecting the finish of containers having a central axis and an open mouth surrounded by an axially facing surface for surface variations that may affect sealing engagement with a container cap, said method comprising the steps of:
  rotating the container about its central axis,
  directing light energy onto the sealing surface of the container from a direction opposed to said sealing surface,
  positioning and orienting an array of light sensitive elements with respect to said axis to receive light energy directly reflected by said sealing surface from said source to said array, and so that said array has an effective field of view limited to an angular portion less than the entire circumference of the container sealing surface,
  scanning said array at increments of container rotation to develop information indicative of intensity of light reflected by said sealing surface onto each said element as a function of said increments, and
  detecting commercial variations in the container sealing surface as a function of said information.

32. The method set forth in claim 31 wherein said array is oriented with respect to said axis to scan in linear fields orthogonal to the sealing surface at said angular portion.

33. The method set forth in claim 32 comprising the additional step of storing said information in two-dimensional memory as a function of array element and scan increment.

34. The method set forth in claim 33 further comprising the step of strobing said light energy at increments of container rotation.

35. Apparatus for inspecting the finish of containers having a central axis and an open mouth surrounded by an axially facing surface for sealing engagement with a container cap, said apparatus comprising:
  means for rotating the container about its central axis,
  a stroboscopic light source positioned to direct light energy onto the sealing surface of a container in said holding-and-rotating means,
  means for strobing said light source at increments of container rotation,
  a camera that includes an array of light sensitive elements positioned and oriented with respect to said axis to receive light energy reflected by said sealing surface, said camera having an effective field of view that includes at least an angular portion of the container sealing surface,
  means for scanning said camera array at increments of container rotation to develop information indicative of intensity of light at each said element as a function of said increments, and
  means for detecting commercial variations in the container sealing surface as a function of said information.

36. The apparatus set forth in claim 35 wherein said camera comprises a linear array camera, and wherein said array is scanned and said light source is strobed at equal increments of container rotation.

37. The apparatus set forth in claim 35 wherein said camera comprises an area array camera, and wherein said scanning means comprises means for scanning a number of rows of said area array at each strobe increment of container rotation.

38. The apparatus set forth in claim 35 wherein said scanning means includes means for storing said information in two-dimensional memory as a function of array element and scan increment.

39. The apparatus set forth in claim 38 wherein said camera array is oriented with respect to said axis and coupled to said scanning means to scan said array in linear fields orthogonal to said axis.

40. The apparatus set forth in claim 35 wherein said stroboscopic light source includes means for focusing a cone of light energy at substantial solid angle onto the container sealing surface within said field of view.

41. A method of inspecting the finish of containers having a central axis and an open mouth surrounded by an axially facing surface for sealing engagement with a container cap, said method comprising the steps of:
  rotating the container about its central axis,
  directing light energy onto the sealing surface of the container,
  strobing said light energy at increments of container rotation,
  positioning and orienting an array of light sensitive elements with respect to said axis to receive light energy reflected by said sealing surface, so that said array has an effective field of view that includes an angular portion of the container sealing surface,
  scanning said array at increments of container rotation to develop information indicative of intensity of light at each said element as a function of said increments, and
  detecting commercial variations in the container sealing surface as a function of said information.

42. The method set forth in claim 41 comprises the additional step of storing said information in two-dimensional memory as a function of array element and scan increment.

43. The method set forth in claim 42 wherein said array is oriented with respect to said axis to scan in linear fields orthogonal to said axis.

* * * * *